US010085673B2

(12) United States Patent
Emtell et al.

(10) Patent No.: US 10,085,673 B2
(45) Date of Patent: Oct. 2, 2018

(54) METHOD FOR CONTINUOUS AND NON-INVASIVE DETERMINATION OF EFFECTIVE LUNG VOLUME AND CARDIAC OUTPUT

(71) Applicant: MAQUET CRITICAL CARE AB, Solna (SE)

(72) Inventors: Par Emtell, Vallingby (SE); Magnus Hallback, Danderyd (SE)

(73) Assignee: MAQUET CRITICAL CARE AB, Solna (SE)

( * ) Notice: Subject to any disclaimer, the term of this patent is extended or adjusted under 35 U.S.C. 154(b) by 1053 days.

(21) Appl. No.: 13/848,304

(22) Filed: Mar. 21, 2013

(65) Prior Publication Data
US 2013/0253359 A1      Sep. 26, 2013

(30) Foreign Application Priority Data

Mar. 21, 2012   (WO) ................. PCT/SE2012/050312

(51) Int. Cl.
*A61B 5/08*     (2006.01)
*A61B 5/00*     (2006.01)
(Continued)

(52) U.S. Cl.
CPC .............. *A61B 5/082* (2013.01); *A61B 5/029* (2013.01); *A61B 5/087* (2013.01); *A61B 5/0836* (2013.01);
(Continued)

(58) Field of Classification Search
USPC ...................................................... 600/532
See application file for complete search history.

(56) References Cited

U.S. PATENT DOCUMENTS 5,495,744 A * 3/1996 Ueda ..................... A61B 5/083
                                                    422/84
5,503,148 A * 4/1996 Pologe ............... A61B 5/14551
                                                    128/925
(Continued)

FOREIGN PATENT DOCUMENTS

JP        2004532672 A     10/2004
WO     WO-02/074166 A1      9/2002
(Continued)

OTHER PUBLICATIONS

Gedeon et al., "A New Method for Noninvasive Bedside Determination of Pulmonary Blood Flow," Medical & Biological Engineering & Computing, vol. 18, pp. 411-418 (1980).
(Continued)

*Primary Examiner* — Jacqueline Cheng
*Assistant Examiner* — Jairo Portillo
(74) *Attorney, Agent, or Firm* — Wesley Scott Ashton

(57) ABSTRACT

In a method for continuous and non-invasive determination of the effective lung volume, the cardiac output, and/or the carbon dioxide content of venous blood of a subject during a sequence of respiratory cycles, the inspiratory and expiratory flow, and the carbon dioxide content of at least the expiration gas are measured. In each respiratory cycle, a first parameter related to the subject's fraction of alveolar carbon dioxide, a second parameter related to the carbon dioxide content of the subject's arterial blood, and a third parameter related to the subject's carbon dioxide elimination are determined based on the measured inspiratory flow, expiratory flow and carbon dioxide content. The effective lung volume, the cardiac output, and/or the carbon dioxide content of venous blood of the subject is determined based on the correlation of the first, second and third parameters.

24 Claims, 4 Drawing Sheets

(51) Int. Cl.
*A61B 5/029* (2006.01)
*A61B 5/083* (2006.01)
*A61B 5/087* (2006.01)
*A61M 16/00* (2006.01)
*G16H 50/50* (2018.01)

(52) U.S. Cl.
CPC .......... *A61B 5/72* (2013.01); *A61M 16/0051* (2013.01); *A61M 16/026* (2017.08); *G16H 50/50* (2018.01); *A61M 2016/0036* (2013.01); *A61M 2230/432* (2013.01)

(56) References Cited

U.S. PATENT DOCUMENTS

| | | | |
|---|---|---|---|
| 5,971,934 A * | 10/1999 | Scherer | A61B 5/0836 128/923 |
| 6,102,868 A | 8/2000 | Banner et al. | |
| 7,074,196 B2 | 7/2006 | Kock et al. | |
| 8,398,559 B2 | 3/2013 | Kock et al. | |
| 2002/0169385 A1 | 11/2002 | Heinonen et al. | |
| 2005/0124907 A1 | 6/2005 | Kuck et al. | |
| 2005/0143640 A1* | 6/2005 | Hoctor | A61B 8/4236 600/407 |
| 2006/0253038 A1 | 11/2006 | Kuck et al. | |
| 2007/0000494 A1 | 1/2007 | Banner et al. | |
| 2009/0105556 A1* | 4/2009 | Fricke | A61B 5/0059 600/301 |
| 2009/0299430 A1 | 12/2009 | Davies et al. | |
| 2010/0056931 A1* | 3/2010 | Soffer | A61B 5/02028 600/486 |
| 2011/0237911 A1* | 9/2011 | Lamego | A61B 5/14551 600/323 |

FOREIGN PATENT DOCUMENTS

| | | |
|---|---|---|
| WO | WO-2006/047212 A1 | 5/2006 |
| WO | WO-2006/11956 A1 | 11/2006 |
| WO | WO-2006/119545 A1 | 11/2006 |

OTHER PUBLICATIONS

Stedman's Medical Dictionary, 1982, 885, Williams & Wilkins, Baltimore, MD, US.

* cited by examiner

METHOD FOR CONTINUOUS AND NON-INVASIVE DETERMINATION OF EFFECTIVE LUNG VOLUME AND CARDIAC OUTPUT

This application claims priority to International Application No. PCT/SE2012/050312, filed Mar. 21, 2012.

BACKGROUND OF THE INVENTION

Field of the Invention

The present invention relates to a method, a computer program and a device for determining physiological parameters related to the effective lung volume, the cardiac output, and/or the carbon dioxide content of venous blood of a subject. In particular, the invention relates to non-invasive and continuous determination of such parameters during ventilatory treatment of a patient, based on measured inspiratory and expiratory flows, and carbon dioxide content of expiration gases.

Description of the Prior Art

Cardiac output (CO) is the rate at which blood is pumped by the heart to the organs of the body. A parameter that is closely related to cardiac output is pulmonary capillary blood flow (PCBF), i.e. the alveolar blood flow. The effective (non-shunt) pulmonary capillary blood flow equals the cardiac output in case of no or neglected cardiac shunt flow. Cardiac output and effective pulmonary capillary blood flow are important measures of cardiovascular stability.

Effective lung volume (ELV) is normally defined as the volume of the lung that takes part in gas exchange, and so is an important measure of the lung function.

Monitoring parameters related to cardiac output and effective lung volume is important when the cardiovascular stability and/or the lung function is potentially threatened, such as during surgery and in critically ill patients. For example, it is often desired to monitor the effective lung volume and sometimes also cardiac output during ventilatory treatment of a patient.

There are several solutions according to prior art for non-invasive determination of parameters relating to cardiac output and/or effective lung volume. Some of these solutions make use of various variations of the carbon dioxide Fick method where the cardiac output of a patient is determined using the following basic relationship:

$$Q = V_{CO2}/(CvCO_2 - CaCO_2),$$

where Q is cardiac output or pulmonary capillary blood flow, $V_{CO2}$ is the volume of carbon dioxide excreted from the body of a patient during respiration (carbon dioxide elimination), $CvCO_2$ is carbon dioxide content of the venous blood of the patient, and $CaCO_2$ is the carbon dioxide content of the arterial blood of the patient.

Typically, a differential form of the carbon dioxide Fick equation is used to non-invasively determine the cardiac output of the patient. Differential Fick techniques are based on the premise that cardiac output and effective pulmonary blood flow can be estimated based on the changes of other measurable parameters when a change in the effective ventilation of the patient occurs. During mechanical ventilation of a patient, such a change in effective ventilation may be effectuated e.g. by varying the degree of rebreathing of expiration gases or by changing the tidal volume, the respiratory rate or the so called insp-hold pause between inspiratory phases and expiratory phases.

EP1257201 discloses an apparatus for non-invasively measuring pulmonary capillary blood flow and cardiac output using known rebreathing techniques. In one embodiment, data on carbon dioxide elimination ($VCO_2$) and data on carbon dioxide content of the arterial blood of the patient ($CaCO_2$) are obtained and a correlation coefficient between the carbon dioxide elimination data and the data on the carbon dioxide content is determined. This correlation coefficient is then used to calculate at least one of the mixed venous carbon dioxide content, the pulmonary capillary blood flow, and the cardiac output.

U.S. Pat. No. 7,699,788 and WO2006047212 disclose methods for non-invasively estimating functional residual capacity or effective lung volume by obtaining carbon dioxide and flow measurements at or near the mouth of a patient. The measurements are obtained during baseline breathing and during and shortly after inducement of a change in the subject's effective ventilation. The obtained measurements are evaluated to determine the amount of time required for exhaled carbon dioxide levels to return to normal—effectively an evaluation of carbon dioxide "washout" from the subject's lungs. Conversely, carbon dioxide and flow measurements may be evaluated to determine the amount of time it takes carbon dioxide to "wash in," or reach peak levels within, the lungs of the subject following the change in the subject's effective ventilation. Measures of the effective lung volume of the patient are then determined from relationships between parameters relating to carbon dioxide elimination and parameters relating to the carbon dioxide content of the arterial blood.

U.S. Pat. No. 6,217,524 describes a method of continuously, non-invasively determining the cardiac output of a patient. The method includes intermittently measuring the cardiac output, the volume of carbon dioxide exhaled by the patient per breath, and determining the arterial-venous gradient of the patient or a similar substantially constant value by dividing the volume of carbon dioxide exhaled by the measured cardiac output. The arterial-venous gradient or similar substantially constant value may then be employed to determine the cardiac output of the patient on a breath-by-breath basis. The carbon dioxide elimination, which is non-invasively measured as the volume of carbon dioxide exhaled by the patient per breath, is divided by the arterial-venous gradient or the substantially constant value to determine the cardiac output. The method may also include generating a signal to compensate for any non-metabolic changes in the carbon dioxide elimination, arterial-venous gradient, or other respiratory or blood gas profile measurements that may be caused by a change in ventilation or breathing of the patient.

Gedeon et al., "Pulmonary blood flow (cardiac output) and volume determined from a short breath hold using the differential Fick method", J. CAIN. MONIT. 17:313-321 (2002), describes a non-invasive method for determining the effective lung volume of a subject using breath-holding techniques. Gedeon et al. also describes equations that relate the pulmonary capillary blood flow of the subject to the subject's effective lung volume. The method is believed to provide inaccurate data as it is based on the assumption that $CO_2$ inflow may not be significantly affected by breath-holding, while breath-holding will cause a change in partial pressure of carbon dioxide. This assumption is inconsistent with the Fick equation, in which carbon dioxide elimination changes linearly with the partial pressure of carbon dioxide while the pulmonary capillary blood flow and the carbon dioxide content of the venous blood ($C_VCO_2$) remain constant.

Peyton et al., "Noninvasive, automated and continuous cardiac output monitoring by pulmonary capnodynamics:

breath-by-breath comparison with ultrasonic flow probe", Anesthesiology 2006 July; 105(1):72-80, describes a technique termed the capnodynamic method for breath-to-breath measurement of pulmonary blood flow from lung carbon dioxide mass balance, using measured carbon dioxide elimination and end-tidal concentration. Here, a capnodynamic equation is used to eliminate the parameter relating to carbon dioxide content of the venous blood of the patient ($C_vCO_2$) in order to obtain resulting equations from which the effective lung volume and the cardiac output can be derived iteratively. To obtain the resulting equations from which the effective lung volume and the cardiac output can be derived, measurements must be made during two substantially equal breaths (two hyperventilated or two hypoventilated breaths) and during two transient breaths (one hyperventilated breath and one hypoventilated breath). This makes the method proposed by Peyton et al. dependent on a certain ventilation pattern.

This capnodynamic method is further described in WO 2006/119546 A1. The method is herein described with reference to a continuous alternating/cyclic alveolar ventilation of a subject, with each period of alveolar ventilation at a particular level (hyperventilation or hypoventilation) constituting a half cycle. Preferably, a cycle comprises 6 to 20 breaths, typically 12 breaths; a half cycle being half of this number of breaths. The method employs a "calibration equation" which has to be solved for breaths that occur at periods in the half cycles during which washing or washout of carbon dioxide is minimized, i.e. for breaths occurring when the carbon dioxide concentration has reached a steady state following a change in effective ventilation.

U.S. Pat. No. 7,135,001 discloses a differential Fick technique for noninvasively determining the pulmonary capillary blood flow or cardiac output of a patient. The technique includes effecting a change-inducing phase in the respiration of the patient, allowing the respiration to return to normal, then immediately repeating the change-inducing phase of respiration. The technique is characterized in that the typical recovery period, where a patient's respiration is allowed to return to normal or baseline levels before again measuring respiratory carbon dioxide and flow is omitted. Thereby, the durations of the normal respiration and change-inducing phases can be abbreviated relative to the time lengths of the corresponding phases in conventional differential Fick techniques. The duration of each phase may be optimized for a patient by evaluating the patient's ventilation but should be within the interval of approximately eighteen to approximately forty-two seconds.

SUMMARY OF THE INVENTION

It is an object of the invention to enable non-invasive determination of parameters relating to the cardiac output and/or the effective lung volume of a subject It is a further object of the invention is to enable simultaneous determination of parameters relating to both the cardiac output and the effective lung volume of a subject.

Yet another object of the invention is to provide a method for continuous monitoring of parameters relating to cardiac output and effective lung volume of a subject undergoing ventilatory treatment, which method is not limited to a certain ventilation pattern.

These and other objects are achieved by a non-invasive method for determining at least one physiological parameter related to the effective lung volume (ELV), the cardiac output (CO), and/or the carbon dioxide content of venous blood ($CvCO_2$) of the subject. The method includes the steps of, during a sequence of respiratory cycles, measuring both an inspiratory flow of inspiration gas inhaled by the subject and an expiratory flow of expiration gas exhaled by the subject, and measuring the carbon dioxide ($CO_2$) content of at least the expiration gas. The method further includes the steps of determining, for each respiratory cycle in the sequence of respiratory cycles, a first parameter related to the fraction of alveolar carbon dioxide ($F_ACO_2$) of the subject, a second parameter related to the carbon dioxide content of the arterial blood ($CaCO_2$) of the subject, and a third parameter related to carbon dioxide elimination ($VCO_2$) of the subject, based on the measured inspiratory flow, expiratory flow and carbon dioxide content. The at least one physiological parameter is then determined based on the correlation of said first, second and third parameters in the sequence of respiratory cycles, typically by solving an overdetermined system of capnodynamic equations, as described below.

In situations where the inspiration gas inhaled by the subject comprises non-negligible amounts of carbon dioxide, e.g. during full or partial rebreathing of expiration gases, the method preferably comprises the steps of measuring also the carbon dioxide content of the inspiration gas, and to take this content into account in the determination of the first, second and third parameters related to $F_ACO_2$, $CaCO_2$ and $VCO_2$, respectively.

The aforementioned method is based on a mathematical model describing the dynamics of ventilation and perfusion of a lung. In a preferred embodiment of the invention, the method employs a capnodynamic equation describing how the fraction of alveolar carbon dioxide, $F_ACO_2$, varies from one respiratory cycle to the next. The capnodynamic equation may be based on a single-compartment lung model or a multi-compartment lung model. In one exemplary embodiment of the invention, the following capnodynamic equation for a single-compartment lung model is used:

$$V \cdot \Delta F_A CO_2 = \Delta t \cdot Q \cdot (CvCO_2 - CaCO_2) - VTCO_2, \quad \text{(Eq. 1)}$$

where V is the effective lung volume of the subject during the respiratory cycle, $\Delta F_ACO_2$ is the change in volume fraction of alveolar carbon dioxide of the subject during the respiratory cycle, $\Delta t$ is the time between two subsequent expirations and so the duration (in time) of a respiratory cycle, Q is the effective or non-shunted pulmonary capillary blood flow (PCBF) of the subject during the respiratory cycle, $CvCO_2$ is the carbon dioxide content of venous blood of the subject during the respiratory cycle, $CaCO_2$ is the carbon dioxide content of arterial blood of the subject during the respiratory cycle, and $VTCO_2$ is the tidal volume elimination of carbon dioxide of the subject, i.e. the volume of carbon dioxide eliminated by the subject during the respiratory cycle.

By measuring the inspiratory and expiratory flows and the carbon dioxide content of the expiration gas during a respiratory cycle, the parameters $\Delta F_ACO_2$, $CaCO_2$ and $VTCO_2$ can be calculated for that respiratory cycle. By calculating these parameters during a sequence of respiratory cycles, each having a predetermined or measurable duration ($\Delta t$), the unknown physiological parameters V, Q and $CvCO_2$, corresponding to the effective lung volume, the effective pulmonary capillary blood flow, and the carbon dioxide content of venous blood of the subject, respectively, can all be determined simultaneously based on the correlation of the parameters $\Delta F_ACO_2$, $CaCO_2$ and $VTCO_2$ in the different respiratory cycles of the analyzed sequence of respiratory cycles. That all of said physiological parameters can be determined simultaneously means that they can all be determined by finding the solution to a single system of capnodynamic equations describing the relationships between said physiological parameters and said first, second and third parameters, as described in greater detail below.

The sequence of respiratory cycles analyzed to determine the physiological parameters V, Q and $CvCO_2$ should comprise more than three respiratory cycles. Calculating the values of the parameters $\Delta F_A CO_2$, $CaCO_2$ and $VTCO_2$ and inserting the parameter values together with the duration of the respiratory cycle ($\Delta t$) into the above equation (Eq. 1) for each respiratory cycle yields an overdetermined system of equations comprising one equation for each respiratory cycle in the analyzed sequence of respiratory cycles. This overdetermined system of equations can then be solved with respect to the unknown physiological parameters V, Q and $CvCO_2$, e.g. using the method of least squares or any other method suitable for finding an approximate solution of an overdetermined system of equations. The solution depends on the correlation between the parameters $\Delta F_A CO_2$, $CaCO_2$ and $VTCO_2$ in the different respiratory cycles.

As understood by the skilled person, the above described calculation relies on the assumption that the physiological parameters V, Q and $CvCO_2$ are substantially constant, or at least that they do not vary too much, during the sequence of analyzed respiratory cycles. It should thus be noted that the calculated values of the physiological parameters V, Q and $CvCO_2$ can be said to represent mean values during the analyzed sequence of respiratory cycles.

By replacing the parameter values of $\Delta F_A CO_2$, $CaCO_2$, $VTCO_2$ and $\Delta t$ for the "oldest" respiratory cycle in the overdetermined system of equations with corresponding parameter values for the most recent respiratory cycle, the effective lung volume, the effective pulmonary capillary blood flow and the carbon dioxide content of venous blood of the subject can be continuously monitored in an effective and reliable manner.

An advantage with the proposed method is that it can be used to determine parameters relating to the effective lung volume, the cardiac output, and the carbon dioxide content of venous blood of the subject simultaneously in an efficient and reliable manner, as they are all given by the solution to a single system of equations.

Another advantage is that the proposed method can be used for any given sequence of respiratory cycles as long as the carbon dioxide content in the expiration gas exhaled by the subject varies slightly during the analyzed sequence of respiratory cycles. The method does not require any particular breaths in the analyzed sequence of respiratory cycles to be identified and compared with each other. Instead, the method treats all breaths (i.e. respiratory cycles) equally and provides updated values for the physiological parameters V, Q and $CvCO_2$ for each respiratory cycle, no matter any change in the effective ventilation of the patient. Thus, the method is independent of the ventilation pattern of the subject.

Preferably, the carbon dioxide content in the expiration gas exhaled by the subject during the analyzed sequence of respiratory cycles should vary with at least 0.5%, and preferably between 0.5-1%. The required variation in carbon dioxide content of the expiration gas during the analyzed sequence of respiratory cycles may occur naturally during supported ventilation of a spontaneously breathing subject. However, there may be a desire to actively induce a variation in carbon dioxide content of the expiration gas over time by introducing a change in the effective ventilation of the subject. Such a change in effective ventilation may be effectuated e.g. by varying the degree of rebreathing of expiration gases exhaled by the subject or by changing the tidal volume, the respiratory rate or the inspiratory pause (often called insp-hold pause) between inspiratory phases and expiratory phases.

If the method is used to continuously monitor physiological parameters of a patient undergoing ventilatory treatment where changes in the effective ventilation are introduced to actively vary the carbon dioxide content in the expiration gas exhaled by the patient, the changes in ventilation are preferably effectuated such that the patient is alternately subjected to hyperventilation and hypoventilation in a manner making the mean ventilation over time correspond to an optimal degree of ventilation of the patient. Preferably, the effective ventilation is changed such that the variation in carbon dioxide content in the expiration gas exhaled by the subject is 0.5-1% during the sequence of analyzed respiratory cycles.

In a refined embodiment of the invention, known variations in the subject's effective lung volume during the analyzed sequence of respiratory cycles may be used to obtain an updated value of the effective lung volume of the subject, which reflects the current effective lung volume of the subject more accurately than the value determined from the correlation analysis. This updated or "current" value of the effective lung volume may be determined based on the differences between the volume of inspired and expired gas in the respiratory cycles of the analyzed sequence of respiratory cycles, and the parameter related to the effective lung volume determined from the correlation analysis.

Yet another advantage with the proposed method is that a priori information providing an a priori value of one or more of the physiological parameters V, Q and $CvCO_2$ may be used to obtain more accurate measures of the unknown quantities. The a priori information may originate from other methods for measuring these physiological parameters, including but not limited to blood gas measurements providing an a priori value of the carbon dioxide content of venous blood ($CVCO_2$) of the subject, a wash-out procedure providing an a priori value of the effective lung volume (V) of the subject, and obtaining the body weight and measuring the heart rate of the subject to provide an a priori value of the cardiac output or effective pulmonary capillary blood flow (Q) of the subject. The a priori information may be used to set a start value for one or more of the parameters V, Q and $CvCO_2$, or to lock one or two of the parameters to known and fix values. In another embodiment, the above discussed overdetermined system of equations is expanded with additional equations comprising a priori values of one or more of the parameters V, Q and $CvCO_2$, as discussed in greater detail in the detailed description following hereinafter.

Preferably, the method further involves a step of calculating an error indicative of the uncertainty in the determination of the physiological parameters. As long as the measurable and/or known data ($\Delta F_A CO2$, $CaCO2$, $VTCO_2$, $\Delta t$, and any additional a priori values of V, Q and $CvCO_2$) are consistent with the mathematical model used, the error will be small. If however, the measurable and/or known data are inconsistent with the model, the error becomes big. In case of a big error, an alarm signal indicating that the mathematical model is currently unreliable may be generated. Preferably, the error is calculated continuously, i.e. on a breath-by-breath basis, and the alarm signal is generated if the uncertainty exceeds a predetermined threshold value.

According to another aspect of the invention, a device capable of performing the above method is provided. To this end, the device comprises at least one flow sensor for measuring, during a sequence of respiratory cycles of a subject, both an inspiratory flow of inspiration gas inhaled by the subject and an expiratory flow of expiration gas exhaled by the subject. It also comprises at least one gas analyzer for measuring the carbon dioxide content of at least the expiration gas exhaled by the subject in each respiratory cycle of the analyzed sequence. Furthermore, the device comprises a control unit configured to determine, in each respiratory cycle in the sequence of respiratory cycles, a first parameter related to carbon dioxide elimination ($VCO_2$) of the subject, a second parameter related to the carbon dioxide content of the arterial blood ($CaCO_2$) of the subject, and a third parameter related to the fraction of alveolar carbon dioxide ($F_ACO_2$) of the subject, based on the measured inspiratory flow, expiratory flow and carbon dioxide content. The control unit is further configured to determine the at least one physiological parameter related to the effective lung volume, the cardiac output, and/or the carbon dioxide content of venous blood of the subject based on the correlation of said first, second and third parameters in the sequence of respiratory cycles.

Although the device may be a stand-alone device exclusively used for monitoring physiological parameters related to the effective lung volume, the cardiac output, and/or the carbon dioxide content of venous blood of a subject, the above described functionality is particularly intended to be incorporated into a breathing apparatus for providing breathing assist to a patient undergoing ventilatory treatment, such as a ventilator or an anesthesia machine.

Preferably, such a breathing apparatus is equipped with a flow sensor and a gas analyzer arranged in or close to a Y-piece connecting an inspiratory branch and an expiratory branch of the breathing apparatus with the patient. The flow sensor may be configured to measure the inspiratory and expiratory flow to and from the patient continuously to obtain a continuous flow curve representing the flow of gas into and out of the airways of the patient over time. Likewise, the gas analyzer may be configured to measure the carbon dioxide content in the inspiration gas and the expiration gas continuously to obtain a continuous $CO_2$ fraction curve representing the carbon dioxide content inhaled and exhaled by the patient over time. A control unit of the breathing apparatus may be configured to use the flow and carbon dioxide content measurements to determine the first, second and third parameters related to $F_ACO_2$, $CaCO_2$ and $VCO_2$, respectively, for each respiratory cycle in the analyzed sequence of respiratory cycles, and to determine the at least one physiological parameter related to the effective lung volume, the cardiac output, and/or the carbon dioxide content of venous blood of the subject based on the correlation of said first, second and third parameters in the sequence of respiratory cycles.

The control unit of the breathing apparatus is further configured to control the ventilation provided to the patient by the breathing apparatus, and is preferably configured introduce a change in the effective ventilation of the patient to ensure that the carbon dioxide content of the expiration gas varies with at least 0.5% and preferably between 0.5% and 1% during the analyzed sequence of respiratory cycles.

The control unit is preferably operable to cause the breathing apparatus to apply a ventilation pattern to the patient comprising a sequence of hyperventilated breaths followed by a sequence of hypoventilated breaths. This ventilation pattern may be applied to the patient during the entire ventilatory treatment, meaning that the patient is always either hyperventilated or hypoventilated. The sequences of hyperventilated and hypoventilated breaths are preferably controlled such that the total ventilation over time corresponds to a desired, optimal ventilation of the patient. In one embodiment, the control unit is operable to cause a change in the duration of the insp-hold-pause between inspiration phases and expiration phases to make the breathing apparatus switch between hyperventilation and hypoventilation.

In other embodiments, to make the breathing apparatus switch between hyperventilation and hypoventilation, the control unit may be operable to cause a change in one or more of the tidal volume of breathing gas delivered to the patient during inspiration, the respiratory rate, and the degree of rebreathing of expiration gases exhaled by the patient.

The logic required to enable the device (a stand-alone device or a breathing apparatus) to carry out the method is preferably implemented by means of software. Thus, according to another aspect of the invention, a computer program for determining at least one physiological parameter related to the effective lung volume, the cardiac output, and/or the carbon dioxide content of venous blood of a subject is provided. The computer program comprises computer readable code which, when executed by a processor of a device configured as described above, causes the device to carry out the inventive method.

Installing such a computer program on existing breathing apparatuses equipped with means for measuring the flow of inspiration and expiration gases and the carbon dioxide content of expiration gases allows existing breathing apparatuses to carry out the inventive method.

DESCRIPTION OF THE PREFERRED EMBODIMENTS

Figure 1:
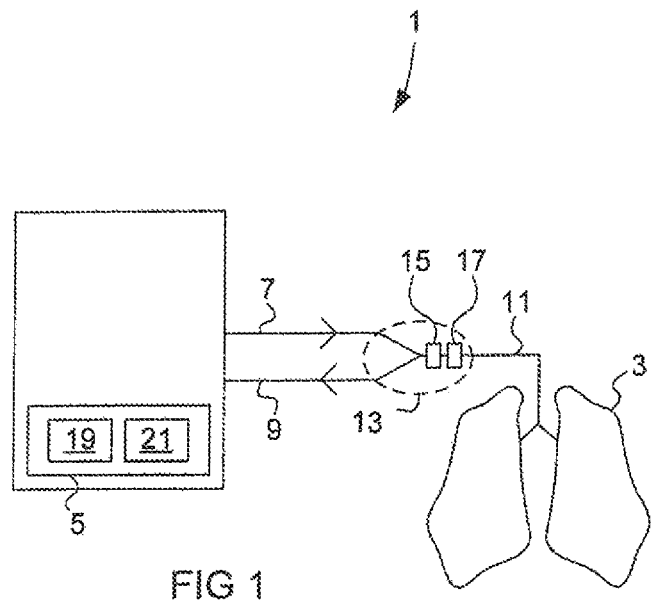
FIG. 1 illustrates a device in form of a breathing apparatus according to an exemplary embodiment of the invention.

FIG. 1 illustrates a device 1 for continuous and non-invasive determination of one or more physiological parameters related to the effective lung volume (ELV), the cardiac output, and/or the carbon dioxide content of venous blood ($CvCO_2$) of a subject 3, according to an exemplary embodiment of the invention.

In this embodiment, the device 1 is a breathing apparatus, such as a ventilator or an anesthesia machine, for providing breathing assist to the subject 3. The breathing apparatus comprises a control unit 5 for controlling the ventilation of the subject based on preset parameters and measurements obtained by various sensors of the breathing apparatus. Furthermore, the breathing apparatus comprises an inspiratory branch 7 for conveying inspiration gases to the subject 3 and an expiration branch 9 for conveying expiration gases away from the patient. The inspiratory and expiratory branches are connected to a patient connector 11 via a Y-piece 13.

A flow sensor 15 and a gas analyzer 17 are arranged in the Y-piece 13 and operable to measure the flows and the carbon dioxide ($CO_2$) content, respectively, of the inspiration and expiration gases to and from the subject 3. The control unit 5 is configured to determine the physiological parameter(s) based on the measurements obtained by the flow sensor 15 and the gas analyzer 17. To this end, the control unit 5 comprises a non-volatile memory 19 storing a computer program that causes the control unit 5 to calculate the physiological parameter(s) according to the principles described below, when executed by a processing unit 21 of the control unit 5. Unless stated otherwise, all steps of the inventive method described hereinafter are performed by the control unit 5 of the device 1 through execution of a computer program.

Figure 2:
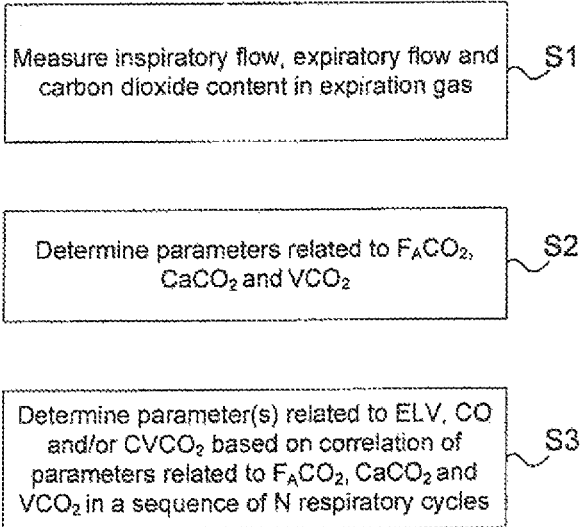
FIG. 2 is a flowchart illustrating the basic principles of the invention.

FIG. 2 illustrates the basic principles of the proposed method for continuous and non-invasive determination of the one or more physiological parameters. In the description of the inventive method following hereinafter, simultaneous reference will be made to the breathing apparatus in FIG. 1.

Each step of the method illustrated in FIG. 2 is performed once for each respiratory cycle of the subject 3. A respiratory cycle comprises an inspiration phase and an expiration phase and the time or duration of a respiratory cycle is typically defined as the time between the end of an expiration phase and the end of the next expiration phase. The duration of the respiratory cycles may vary depending on the mode of ventilation and/or the ventilation pattern provided by the breathing apparatus.

In a first step, S1, the inspiratory flow and the expiratory flow, as well as the carbon dioxide content of at least the expiration gas but preferably also the inspiration gas are measured by the flow sensor 15 and the gas analyzer 17.

In a second step, S2, a first parameter related to the fraction of alveolar carbon dioxide ($F_ACO_2$) of the subject 3, a second parameter related to the carbon dioxide content of the arterial blood ($CaCO_2$) of the subject 3, and a third parameter related to carbon dioxide elimination ($VCO_2$) of the subject 3, are determined based on the measurements received from the flow sensor 15 and the gas analyzer 17.

In a third and last step, S3, the at least one physiological parameter related to the effective lung volume, the cardiac output, and/or the carbon dioxide content of venous blood of the subject 3 is determined based on the correlation of the first, second and third parameters determined in step S2 in a sequence of N respiratory cycles. The sequence of respiratory cycles is preferably but not necessarily a sequence of consecutive respiratory cycles comprising the last completed respiratory cycle and the N−1 immediately preceding respiratory cycles.

The number of respiratory cycles, N, in the sequence on which the correlation analysis is performed is preferably fixed. When using a preferred mathematical model described in more detail below, the number of respiratory cycles in the analyzed sequence should be more than three. By analyzing more than three respiratory cycles, all three parameters related to the effective lung volume, the cardiac output, and the carbon dioxide content of venous blood of the subject 3 can be determined from the relationships between the three dimensional data points defined by the values of the first, second and third parameter in each respiratory cycle.

The first parameter determined in step S2 and related to the fraction of alveolar carbon dioxide is preferably the change in volume fraction of alveolar carbon dioxide of the subject during the respiratory cycle, i.e. the difference in volume fraction of alveolar carbon dioxide ($\Delta F_ACO_2$) between the current respiratory cycle and the preceding respiratory cycle. This parameter may be estimated from the measured fraction of carbon dioxide in the expiration gas, e.g. as the difference between the end-tidal carbon dioxide fractions ($FetCO_2$) in the current previous respiratory cycle and the previous respiratory cycle.

The second parameter determined in step S2 and related to the carbon dioxide content of the arterial blood is preferably the carbon dioxide content of the arterial blood ($CaCO_2$) itself, measured in $[mL_{CO2,gas}/L_{blood}]$. As well known in the art, $CaCO_2$ can be calculated from a $CO_2$ dissociation curve function for the solubility of carbon dioxide in arterial blood. $CaCO_2$ is assumed to depend on the partial pressure of carbon dioxide in the arterial blood ($PaCO_2$), which may be approximated as the partial alveolar pressure of carbon dioxide ($P_ACO_2$), which in turn can be derived from the fraction of alveolar carbon dioxide ($F_ACO_2$) and the barometric pressure ($P_ACO_2 = P_{bar} \cdot F_ACO_2$). The dissociation curve function can then be determined e.g. using equations 6 and 8 in Capek J M, Roy R J, "Noninvasive measurement of cardiac output using partial CO2 rebreathing", IEEE Trans Biomed Eng 1988; 35: 653-61.

The third parameter determined in step S2 and related to carbon dioxide elimination is preferably the tidal elimination of carbon dioxide ($VTCO_2$), measured in $[mL_{CO2,gas}]$. This parameter may be derived from the measured inspiratory and expiratory flows and the measured carbon dioxide content of the inspiratory and expiratory gas by integrating the flow curve ($\varnothing(t)$) obtained by means of the flow sensor 15, and the carbon dioxide fraction curve ($FCO_2(t)$) obtained by means of the gas analyzer 17, during the respiratory cycle. The tidal elimination of carbon dioxide may hence be calculated as:

$$VTCO_2 = \int_{t_{ee}-\Delta t}^{t_{ee}} \varnothing(t) \cdot FCO_2(t) dt$$

where $t_{ee}$ is the point in time where the expiration phase ends (the end-expiratory time) and $\Delta t$ is the duration of the respiratory cycle. The flow curve $\varnothing(t)$ is here defined as positive in the direction of expiratory flow. Unless the subject is ventilated using rebreathing techniques or by means of a breathing apparatus having a significant dead volume, the carbon dioxide content in the inspiration gas is very low and can be ignored. In this case, it is not necessary to measure the carbon dioxide content of the inspiration gas inhaled by the subject.

To determine the unknown physiological parameters related to the effective lung volume, the cardiac output, and/or the carbon dioxide content of venous blood of the subject, the method preferably employs the following capnodynamic equation for a single-chamber lung model, which describes how the fraction of alveolar carbon dioxide ($F_ACO2$) varies from one respiratory cycle to the next:

$$V \cdot \Delta F_ACO_2 = \Delta t \cdot Q \cdot (CvCO_2 - CaCO_2) - VTCO_2, \quad (Eq. 1)$$

where V is the effective lung volume of the subject during the respiratory cycle, $\Delta F_ACO_2$ is the change in volume fraction of alveolar carbon dioxide of the subject during the respiratory cycle, $\Delta t$ is the time between two subsequent expirations and so the duration (in time) of a respiratory cycle, Q is the effective pulmonary capillary blood flow (PCBF) of the subject during the respiratory cycle, $CvCO_2$ is the carbon dioxide content of venous blood of the subject during the respiratory cycle, $CaCO_2$ is the carbon dioxide content of arterial blood of the subject during the respiratory cycle, and $VTCO_2$ is the tidal volume elimination of carbon dioxide of the subject, i.e. the volume of carbon dioxide eliminated by the subject during the respiratory cycle.

Introducing an index 'k' indicating the number of the respiratory cycle in the analyzed sequence of respirator cycles, and rearranging Equation 1 such that the unknown parameters are gathered on the left-hand side of the equation yields:

$$V \cdot \Delta F_A CO_2^k - Q \cdot CvCO_2 \cdot \Delta t^k + Q \cdot CaCO_2^k \cdot \Delta t^k = -VTCO_2^k \quad \text{(Eq. 2)}$$

Writing this equation in matrix form for the respiratory cycles $k=1, 2, \ldots, N$ in the analyzed sequence of respiratory cycles yields:

$$\begin{bmatrix} \Delta F_A CO_2^1 & -\Delta t^1 & (CaCO)_2^1 \cdot \Delta t^1 \\ \vdots & \vdots & \vdots \\ \Delta F_A CO_2^k & -\Delta t^k & (CaCO)_2^k \cdot \Delta t^k \\ \vdots & \vdots & \vdots \\ \Delta F_A CO_2^N & -\Delta t^N & CaCO_2^N \cdot \Delta t^N \end{bmatrix} \cdot \begin{bmatrix} V \\ Q \cdot CvCO_2 \\ Q \end{bmatrix} = \begin{bmatrix} -VTCO_2^1 \\ \vdots \\ -VTCO_2^k \\ \vdots \\ -VTCO_2^N \end{bmatrix} \quad \text{(Eq. 3)}$$

When the analyzed sequence of respiratory cycles N comprises more than three breaths (i.e when N>3), this becomes an overdetermined system of equations and the unknown parameter triplet $\{V, Q \cdot CvCO_2, Q\}$ and hence the physiological parameters V, Q, and $CvCO_2$ relating to the effective lung volume, the cardiac output, and the carbon dioxide content of venous blood of the subject, respectively, can be determined by finding an approximate solution to the overdetermined system of equation. As well known in the art, the approximate solution to an overdetermined system of equations can be calculated in different ways, e.g. using the method of least squares. No matter which method is used, the solution to the overdetermined system of equations will depend on the correlation of the parameters $\Delta F_A CO_2$, $CaCO_2$ and $VTCO_2$ in the respiratory cycles of the analyses sequence of respiratory cycles.

This system of equations (Eq. 3) may be rewritten as $A \cdot x_A = a$, where $$A = \begin{bmatrix} \Delta F_A CO_2^1 & -\Delta t^1 & CaCO_2^1 \cdot \Delta t^1 \\ \vdots & \vdots & \vdots \\ \Delta F_A CO_2^k & -\Delta t^k & CaCO_2^k \cdot \Delta t^k \\ \vdots & \vdots & \vdots \\ \Delta F_A CO_2^N & -\Delta t^N & CaCO_2^N \cdot \Delta t^N \end{bmatrix},$$

$$x_A = \begin{bmatrix} V \\ Q \cdot CvCO_2 \\ Q \end{bmatrix}, \text{ and } a = \begin{bmatrix} -VTCO_2^1 \\ \vdots \\ -VTCO_2^k \\ \vdots \\ -VTCO_2^N \end{bmatrix}$$

An approximate solution for the parameter triplet $\{V, Q \cdot CvCO_2, Q\}$ can then be determined by minimizing the error $|A \cdot x_A - a|$. Using the method of least squares, the solution may be calculated as:

$$x_A = (A^T \cdot A)^{-1} \cdot A^T \cdot a \quad \text{(Eq. 4)}$$

In another embodiment, the basic capnodynamic equation (Eq. 1) may be modified by dividing each term thereof with the duration of the respiratory cycle, $\Delta t$, to obtain the following adjusted capnodynamic equation:

$$V \cdot (\Delta F_A CO_2/\Delta t)^k - Q \cdot CvCO_2 + Q \cdot CaCO_2^k = -(VTCO_2/\Delta t)^k, k=1,2,\ldots,N \quad \text{(Eq. 5)}$$

Writing this equation in matrix form for the respiratory cycles $k=1, 2, \ldots, N$ in the analyzed sequence of respiratory cycles yields:

$$\underbrace{\begin{bmatrix} \Delta F_A CO_2^1/\Delta t^1 & -1 & CaCO_2^1 \\ \vdots & \vdots & \vdots \\ \Delta F_A CO_2^k/\Delta t^k & -1 & CaCO_2^k \\ \vdots & \vdots & \vdots \\ \Delta F_A CO_2^N/\Delta t^N & -1 & CaCO_2^N \end{bmatrix}}_{\tilde{A}} \cdot \underbrace{\begin{bmatrix} V \\ Q \cdot CvCO_2 \\ Q \end{bmatrix}}_{\tilde{x}_A} = \underbrace{\begin{bmatrix} -VTCO_2^1/\Delta t^1 \\ \vdots \\ -VTCO_2^k/\Delta t^k \\ \vdots \\ -VTCO_2^N/\Delta t^N \end{bmatrix}}_{\tilde{a}} \quad \text{(Eq. 6)}$$

Using the method of least squares, the optimal solution to this overdetermined system of equations (Eq. 6) can be calculated as:

$$\tilde{x}_A = (\tilde{A}^T \cdot \tilde{A})^{-1} \cdot \tilde{A}^T \cdot \tilde{a} \quad \text{(Eq. 7)}$$

In the case where the duration, $\Delta t$, of the analyzed respiratory cycles varies, the division by $\Delta t^k$ implies a re-weighting of the contribution of the respective respiratory cycle to the overall solution. This means that $\tilde{x}_A$ (Eq. 7) will differ slightly from $x_A$ (Eq. 4) if $\Delta t$ varies in the analyzed sequence of respiratory cycles.

Thus, in order to ensure that all respiratory cycles in the analyzed sequence, N, of respiratory cycles is given equal weight, the basic capnodynamic equation (Eq. 1) is advantageous compared to the modified capnodynamic equation (Eq. 5).

Figure 3A:
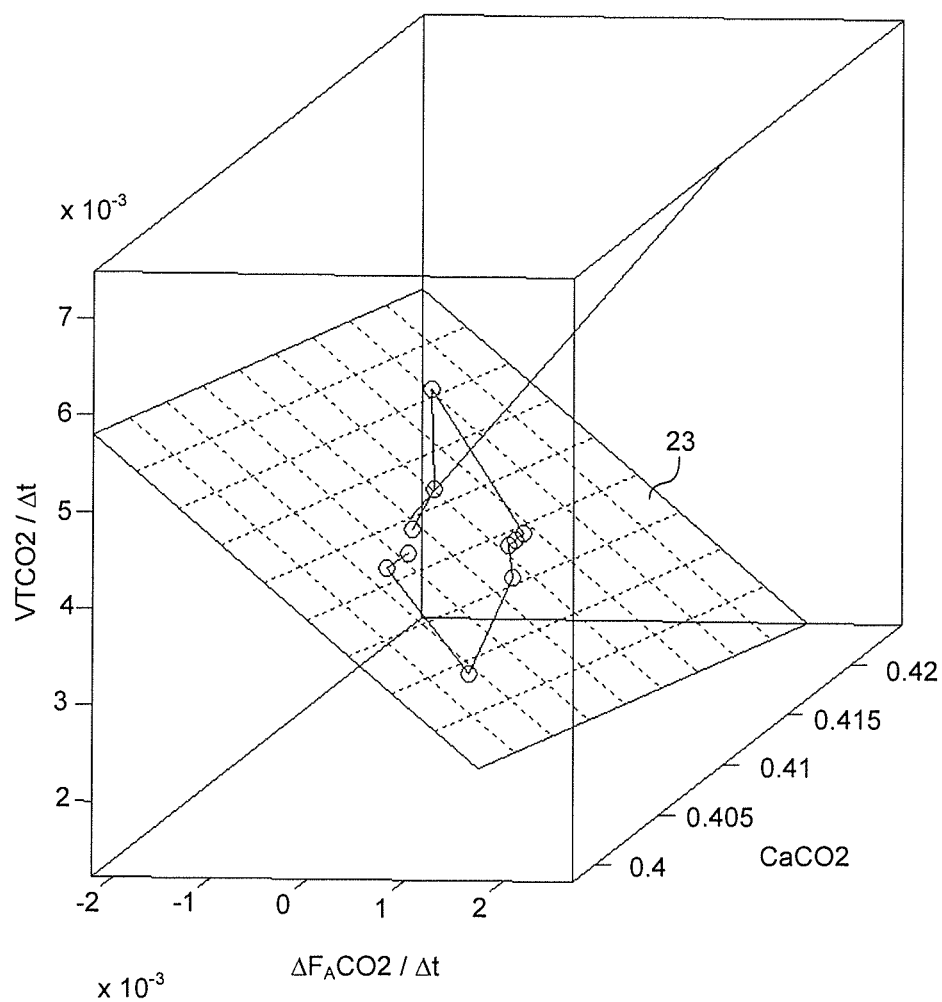
FIGS. 3A and 3B illustrate a visualization of a solution to an overdetermined equation system which is solved to determine the unknown physiological parameters according to an embodiment of the invention.
Figure 3B:
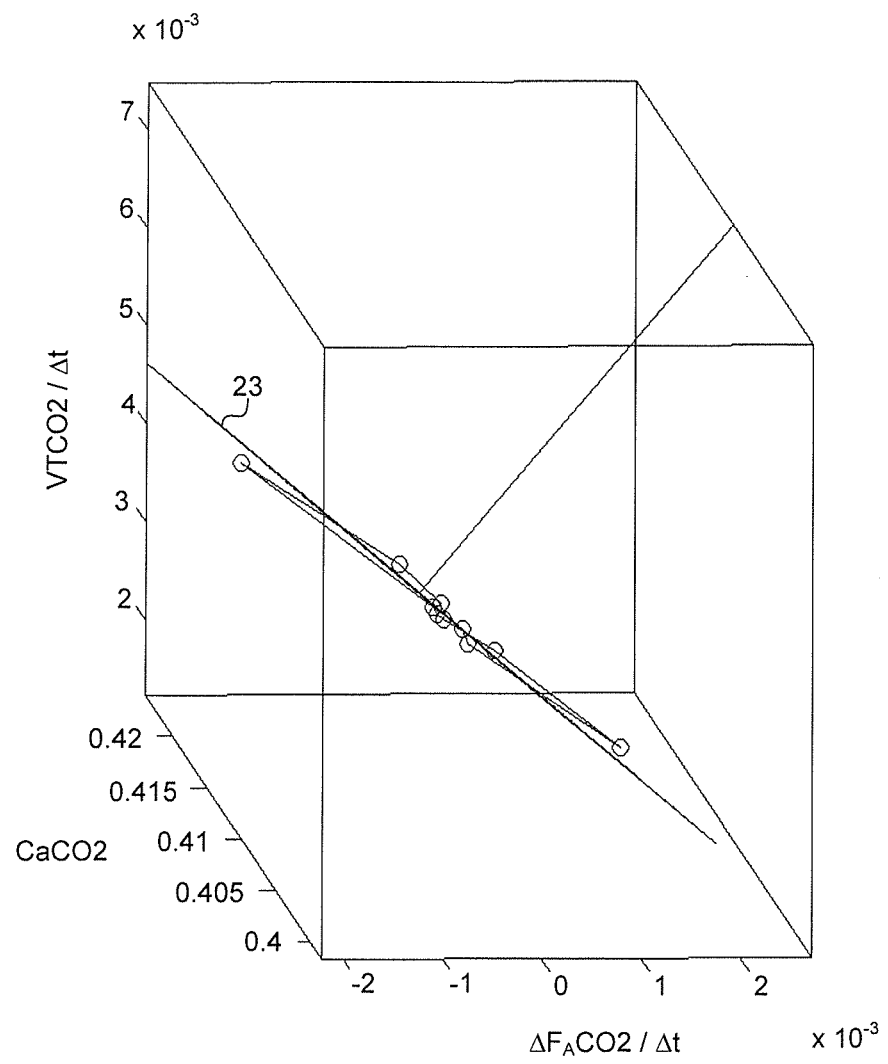

For each respiratory cycle, the parameter triplet $\{\Delta F_A CO2/\Delta t, CaCO2, VTCO2/\Delta t\}$ define a data point in a three dimensional space spanned by said parameter triplet, and the solution to the overdetermined system of equations can be visualized in form of a plane that is fitted to the data points from the analyzed sequence of respiratory cycles in this three dimensional space. Such a plane 23 is illustrated in FIGS. 3A and 3B, wherein the data points defined by the parameter triplet $\{\Delta F_A CO2/\Delta t, CaCO2, VTCO2/\Delta t\}$ for each respiratory cycle is represented by a circle. FIG. 3A illustrates a perspective view of the plane 23, and FIG. 3B illustrates a cross-sectional view of the plane 23 in said three dimensional space. The unknown physiological parameters V and Q define the normal direction to the plane in the three dimensional space, and the parameter $Q \cdot CvCO_2$ defines the translation of the plane along the $VTCO2/\Delta t$ axis. The unknown physiological parameters V, Q and $CvCO_2$ can hence be said to be determined by fitting a plane to a plurality of 3D data points, where each data point is given by the values of the parameter triplet $\{\Delta F_A CO2/\Delta t, CaCO2, VTCO2/\Delta t\}$ for a respective respiratory cycle in the analyzed sequence, N, of respiratory cycles.

In order to obtain a more accurate value of the current effective lung volume of the subject, the model may be adjusted to take known variations in the subject's effective lung volume during the analyzed sequence of respiratory cycles into account. The control unit 5 is preferably configured to calculate the volume of inspiration gas inhaled by the subject 3 in each inspiration phase and the volume of expiration gas exhaled by the subject in each expiration phase. This may be achieved by integrating the inspiration and expiration flows measured by the flow sensor 15. Thereby, a difference $\Delta V$ between the inhaled gas volume, VTi, and the exhaled gas volume, VTe, for each respiratory cycle can be determined as $\Delta V = VTi - VTe$. Then, for a given respiratory cycle n in the sequence of analyzed respiratory cycles, the end-expiratory lung volume of that respiratory cycle can be expressed as:

$$V^n = V + \Sigma_{j=1}^n \Delta V^j, \quad (\text{Eq. 8})$$

where $V^n$ is the end-expiratory lung volume of the subject in respiratory cycle n, V is the end-expiratory lung volume of the subject in the respiratory cycle immediately preceding the analyzed sequence of respiratory cycles, and $\Delta V^j$ is the difference in end-expiratory volume between a respiratory cycle j and an immediately preceding respiratory cycle.

Thus, all end-expiratory lung volumes in the analyzed sequence of respiratory cycles can be expressed as parts of an unknown end-expiratory volume V of the respiratory cycle immediately preceding the analyzed sequence. By inserting $V^n$ in the basic capnodynamic equation (Eq. 1), the right-hand side of Equation 2 can be expressed as follows:

$$-VTCO_2^n \Rightarrow -VTCO_2^n + \Delta F_A CO_2^n \Sigma_{j=1}^n \Delta V^j + \Delta V^n F_A CO_2^{n-1} \quad (\text{Eq. 9})$$

In this way, a fast update of the current effective lung volume of the subject (i.e. the effective lung volume of the latest respiratory cycle, corresponding to respiratory cycle number N in the analyzed sequence of respiratory cycles) can be obtained by calculating the effective lung volume $V^N$ of the last respiratory cycle in the analyzed sequence of respiratory cycles from the approximate value of the effective lung volume V obtained by solving the above overdetermined system of equations (Eq. 3 or Eq. 6). The effective lung volume $V^N$ of the most recent respiratory cycle can then be determined as:

$$V^N = V + \Sigma_{j=1}^N \Delta V^j \quad (\text{Eq. 10})$$

The approximation of the effective lung volume V obtained by solving the above overdetermined system of equations (Eq. 3 or Eq. 6) must be interpreted as "the best mean value" of the effective lung volume of the subject during the analyzed sequence of respiratory cycles 1 to N. Using the proposed addition of taking known variations in the subject's effective lung volume into account (Equations 8-10) means that the unknown physiological parameters Q and $CvCO_2$ relating to the cardiac output and the carbon dioxide content of venous blood of the subject, respectively, are assumed to be substantially constant during the analyzed sequence of respiratory cycles, while the effective lung volume V of the subject is allowed to vary from breath to breath (i.e. from one respiratory cycle to another).

In the above example of compensation for variations in effective lung volume, the approximation of the effective lung volume V obtained by solving the overdetermined system of equations (Eq. 3 or Eq. 6) is assumed to correspond to the effective lung volume of the subject in the respiratory cycle immediately preceding the analyzed sequence of respiratory cycles. Of course, it is also possible to assume that the calculated approximation V corresponds to the effective lung volume of the last respiratory cycle in the sequence of analyzed respiratory cycles, and to count "backwards" to determine the effective lung volume of each respiratory cycle in the analyzed sequence taking the difference between the volumes of inhaled inspiration gas and exhaled expiration gas into account. As understood by the skilled person, this requires the expression for $VTCO_2$ (Eq. 9) to be modified accordingly.

In order to calculate more accurate approximations of the physiological parameters V, Q and $CvCO_2$, the mathematical model may be adjusted by incorporation of a priori information on one or more of these physiological parameters. The a priori information may comprise one or more values of one or more of the physiological parameters. Such values may be obtained through other methods of measurement, by estimating the values based on physiological information about the subject, or from the analysis of one or more sequences of respiratory cycles preceding the sequence of respiratory cycles to be analyzed using the method described herein.

For example, an a priori value of the carbon dioxide content of venous blood ($CvCO_2$) of the subject may be obtained from blood gas measurements, as well known in the art. An a priori value of the effective pulmonary capillary blood flow of the subject 3 may be estimated based on the body weight and the heart rate of the subject, as suggested e.g. by Jegier et al. in Br Heart J. 1963 July; 25(4): 425-430. A priori values of the physiological parameters may be provided to the control unit 15 of the device 1 through user input on a user interface of the device 1 (not shown). An a priori value of the effective lung volume (V) of the subject can be determined from a wash-out process, as also well known in the art. To this end, the control unit 15 of the device in FIG. 1 may be adapted to effectuate a wash-out process according to prior art for determining the effective lung volume V of the subject 3, prior to determination of the physiological parameters V, Q and $CvCO_2$ by means of the method described herein.

The a priori information may be incorporated into the mathematical model by expanding the above described system of equations through addition of one equation for each unknown parameter V, Q and $CvCO_2$. For example, the system of equations can be written as:

$$V \cdot \Delta F_A CO_2^k - Q \cdot CvCO_2 \cdot \Delta t^k + Q \cdot CaCO_2^k \cdot \Delta t^k = VtCO_2^k,$$
$$k = 1, 2 \ldots N \quad (\text{Eq. 2})$$

$$V \cdot w_1 = V_{apriori} \cdot w_1 \quad (\text{Eq. 11})$$

$$(Q \cdot CvCO_2) \cdot w_2 = Q \cdot CvCO_{2apriori} \cdot w_2 \quad (\text{Eq. 12})$$

$$Q \cdot w_3 = Q_{apriori} \cdot w_3, \quad (\text{Eq. 13})$$

where $w_1$, $w_2$ and $w_3$ are weighting coefficients that give different weights to the additional equations (Eq. 11 to Eq. 13) dependent on the size of the coefficients in relation to the norm of the matrix A (or Ã) as defined above. The additional equations can be re-written on matrix form as:

$$\underbrace{\begin{bmatrix} w_1 & 0 & 0 \\ 0 & w_2 & -CvCO_{2apriori} \cdot w_2 \\ 0 & 0 & w_3 \end{bmatrix}}_{R} \cdot \underbrace{\begin{bmatrix} V \\ Q \cdot CvCO_2 \\ Q \end{bmatrix}}_{x_C} = \underbrace{\begin{bmatrix} V_{apriori} \cdot w_1 \\ 0 \\ Q_{apriori} \cdot w_3 \end{bmatrix}}_{b} \quad (\text{Eq. 14})$$

The total system of equations is then given by:

$$\underbrace{\begin{bmatrix} A \\ \hline B \end{bmatrix}}_{C} \cdot x_C = \underbrace{\begin{bmatrix} a \\ \hline b \end{bmatrix}}_{c}, \quad \text{(Eq. 15)}$$

which can be solved with respect to the parameter triplet $\{V, Q \cdot CvCO_2, Q\}$, e.g. using the method of least squares:

$$x_C \leq (C^T \cdot C)^{-1} \cdot C^T \cdot c \quad \text{(Eq. 16)}$$

Preferably, the method further comprises the step of calculating an error indicating the uncertainty in the determination of the one or more physiological parameters. Using the basic capnodynamic model (Eq. 1) described above as an example, the error, $E_A$, can be determined as the error in the best fit of ($x_C$) to the model:

$$E_A = (A \cdot x_C - a)^T \cdot (A \cdot x_C - a), \quad \text{(Eq. 17)}$$

An error, $E_{\Delta FACO2}$, that is easier to interpret can be determined by normalizing Equation 3 with V. In this way, the system of equations $Ax/V = a/V$ becomes dimensionless and contains terms that should balance the change in volume fraction of alveolar carbon dioxide ($\Delta F_A CO_2$) of the subject during the respiratory cycles:

$$E_{\Delta FACO_2} = \left(\frac{A \cdot x_C - a}{V}\right)^T \cdot \left(\frac{A \cdot x_C - a}{V}\right), \quad \text{(Eq. 18)}$$

In another embodiment, an error can be determined for the expanded capnodynamic model (Eq. 15) comprising the additional "a priori" equations (Eq. 11-13):

$$E_C = (C \cdot x_C - c)^T \cdot (C \cdot x_C - c), \quad \text{(Eq. 19)}$$

As long as the values of the input parameters ($\Delta F_A CO_2$, $VTCO_2$, $\Delta t$, $CaCO_2$) and any additional a priori values of V, $CvCO_2$ or Q fit well to the proposed lung model, the error will be small. If the error is big, however, this indicates that the model is not optimally adapted to the prevailing circumstances. For example, a big error may be an indication that some of the unknown physiological parameters that are assumed to be substantially constant during the analyzed sequence of respiratory cycles ($CvCO_2$, Q and in some embodiments also V) actually varies. A big error may also be an indication that the flow sensor 15 or gas analyzer 17 malfunctions, or that some other requirement that must be fulfilled in order for the model to properly reflect the reality is not fulfilled. If the calculated error exceeds a predetermined threshold value, an alarm signal indicating that the model is currently inconsistent with observed data may be generated and provided visually or aurally to an operator of the device 1 serving to monitor the physiological parameters of the subject 3.

It should be appreciated that the error as calculated according to any of the above described principles, just like the determined values of physiological parameters V, $CvCO_2$ and Q, will depend on the correlation between the data points defined by the values of $\Delta F_A CO_2$, $VTCO_2$ and $CaCO_2$ in the respiratory cycles of the analyzed sequence of respiratory cycles.

With reference again to FIG. 1, the control unit 5 of the breathing apparatus is preferably operable to change the effective ventilation of the subject 3 during the sequence of analyzed respiratory cycles so as to cause a change in the carbon dioxide content in the expiration gas exhaled by the subject of at least 0.5% during said sequence. A change in carbon dioxide content in the expiration gas means that some or all of the parameters $F_A CO2$, $CaCO2$, $\Delta t$ and $VTCO2$ varies during the analyzed sequence of respiratory cycles, which is a requirement in order to solve the above discussed overdetermined systems of equations with respect to the unknown physiological parameters. Preferably, the control unit is configured to cause a change in carbon dioxide content in the expiration gas of 0.5%-1% during the analyzed sequence of respiratory cycles.

An advantage with the inventive method as compared to other methods for determining effective lung volume, cardiac output or carbon dioxide content of venous blood of a subject is that it is independent of the type of change in ventilation, and independent of the ventilation pattern provided to the subject. The following is a list of non-exclusive examples of how the change in effective ventilation of the subject may be effectuated by the control unit 5:

1) by varying the tidal volume delivered to the subject 3
2) by varying the respiratory rate of the subject 3
3) by varying the so called insp-hold pause between inspiratory phases and expiratory phases,
4) by varying the degree of rebreathing of expiration gases exhaled by the subject 3 by means of partial rebreathing through a so called NICO loop (NICO—Non-Invasive Cardiac Output)
5) by varying the degree of rebreathing of expiration gases exhaled by the subject 3 by means of partial rebreathing through the inspiratory branch 7 of the breathing apparatus An advantage with the techniques 3 to 5 is that the expiration phase of the respiratory cycle is unaffected using these techniques, which is particularly advantageous as the inventive method relies on measurements of the $CO_2$ content in expiration gas exhaled by the subject and so requires sampling of the $CO_2$ content during the expiratory phases. An advantage with the techniques 1-3 is that most breathing apparatuses (e.g. ventilators) of today can be adapted to carry out the techniques merely by updating the software controlling the operation of the breathing apparatus. The techniques 4-5, on the other hand, typically require use of hardware components not normally included in breathing apparatuses.

As previously mentioned, the control unit 5 is preferably configured to continuously monitor the physiological parameters V, $CvCO_2$ and Q of the subject 3 during the respiratory treatment provided by the breathing apparatus, which may require a repetitive change in the effective ventilation of the subject in order for the carbon dioxide content in the expiration gas to change during each analyzed sequence of respiratory cycles. In order to achieve a desired total ventilation of the subject, the control unit 5 is preferably configured to vary the effective ventilation of the subject 3 such that the subject is alternately subjected to hyperventilation and hypoventilation in a manner making the mean ventilation over time correspond to an optimal degree of ventilation of the patient. This means that a change in the effective ventilation of the subject is always directly followed by a change in the "opposite direction"—there is no baseline ventilation (i.e. "normal" ventilation) of the subject in between the hyperventilation phases and the hypoventilation phases.

To this end, the control unit 5 may be configured to determine, based on ventilation parameters input to the breathing apparatus by an operator and indicating a desired baseline ventilation to be provided to the subject, an optimal ventilation pattern in form of a sequence of hyperventilated and hypoventilated breaths, which ventilation pattern gives the same effect in terms of ventilation as the desired baseline ventilation. For example, the ventilation parameters input by the operator may comprise a parameter indicating a desired minute ventilation of the subject, whereby the control unit may be configured to determine a sequence of hyperventilated and hypoventilated breaths together resulting in said desired minute ventilation. The sequence of hyperventilated and hypoventilated breaths is then continuously repeated throughout the ventilatory treatment, meaning that a new sequence starts directly after the last breath of a previous sequence.

An example of a ventilation pattern that has been found suitable when the analyzed sequence of respiratory cycles comprises ten breaths (i.e. N=10) is a ventilation pattern comprising continuous alternations between five hypoventilated breaths and five hypoventilated breaths. In a preferred embodiment, this ventilation pattern is generated by changing the duration of the insp-hold-pause between inspiratory phases and expiratory phases. For five breaths, the insp-hold-pause is shortened compared to a "normal" insp-hold-pause that would result in a desired baseline ventilation of the subject, so as to deliver five hyperventilated breaths to the subject, and for the following five breaths the insp-hold-pause is prolonged compared to said "normal" insp-hold-pause, so as to deliver five hypoventilated breaths. This pattern may be repeated as long as there is a desire to monitor the physiological parameters using the inventive method described herein. As mentioned above, the durations of the "shortened" and "prolonged" insp-hold-pauses are preferably selected to make the minute ventilation of the subject correspond to the minute ventilation that would have been obtained using the desired baseline ventilation.

Preferred Ventilation Pattern

As previously mentioned, the above described method as well as most methods described in the background portion of this application typically require a repetitive change in the effective ventilation of the subject in order to determine the unknown physiological parameters related to the subject's effective lung volume, cardiac output, and/or carbon dioxide content of venous blood. Notwithstanding the above example in which such a repetitive change in effective ventilation is achieved by means of a ventilation pattern comprising alternating sequences of five hyperventilated breaths and five hypoventilated breaths, more recent research has shown that it is possible and advantageous to use a ventilation pattern with shorter sequences of increased and decreased ventilation. Preferably, the repetitive changes in effective ventilation of the subject are achieved by means of a cyclic ventilation pattern wherein each cycle comprises a first number of breaths of increased ventilation and a second number of breaths of decreased ventilation, where the total number of breaths in each cycle is five or less.

Thus, according to another aspect of the invention, there is provided a non-invasive method for determining at least one physiological parameter related to the effective lung volume, the cardiac output, and/or the carbon dioxide content of venous blood of a subject, including the steps of:

ventilating the subject using a cyclic ventilation pattern wherein each cycle comprises a first number of breaths of increased ventilation and a second number of breaths of decreased ventilation, measuring an inspiratory flow of inspiration gas inhaled by the subject, an expiratory flow of expiration gas exhaled by the subject, and the carbon dioxide content of at least the expiration gas, and determining said at least one physiological parameter from the measured flows and carbon dioxide content, wherein the total number of breaths in each cycle of the cyclic ventilation pattern is five or less.

The cycles of the proposed ventilation pattern are hence shorter than the cycles of the ventilation patterns used for the same purpose in methods according to prior art. The proposed cyclic ventilation pattern has at least the following advantages compared to ventilation patterns having longer sequences of increased and decreased ventilation:

The effective ventilation of the subject is changed at a higher frequency which makes it possible to determine the physiological parameters related to the effective lung volume, the cardiac output, and/or the carbon dioxide content of venous blood of the subject from a shorter sequence of breaths. This reduces the response time in the monitoring of the physiological parameter(s).

The short sequences of increased and decreased ventilation reduce the risk of introducing variations in the carbon dioxide content of the venous blood, $CvCO_2$, of the subject, which risk is particularly high at high levels of cardiac output. Most methods, including the method described in this application, are based on the assumption that $CvCO_2$ is substantially constant during the analyzed sequence of breaths and, consequently, variations in $CvCO_2$ during the analyzed sequence of breaths may introduce errors in the determination of the physiological parameter(s).

The short sequences of increased and decreased ventilation reduce potentially adverse effects on the patient caused by the changes in effective ventilation. For example, in embodiments where breaths of decreased ventilation are generated by prolonging the inspiratory pause compared to the inspiratory pause of breaths of increased ventilation, the periods of increased pressure in the subject's lungs are shortened, which mitigates the risk of adversely affecting the hemodynamics of the subject.

Preferably, for reasons described above, the breaths of increased ventilation are hyperventilated breaths (i.e. breaths of increased ventilation compared to a desired baseline ventilation of the subject) while the breaths of decreased ventilation are hypoventilated breaths (i.e. breaths of decreased ventilation compared to a desired baseline ventilation).

The determination of the at least one physiological parameter is preferably made using an algorithm which does not require a steady state of carbon dioxide content in the expiration gas exhaled by the subject since the sequences of increased and decreased ventilation in the proposed ventilation pattern generally are too short in order for the carbon dioxide content to reach a steady state level.

Preferably, the determination of the physiological parameter(s) is made using the above described method of analyzing the correlation between parameters that are derivable from the measured quantities. Thus, in one embodiment, the method includes the steps of:

ventilating the subject using a cyclic ventilation pattern wherein each cycle comprises a first number of breaths of increased ventilation and a second number of breaths of decreased ventilation, wherein the total number of breaths in each cycle of the cyclic ventilation pattern is five or less, and, during a sequence of breaths:

measuring an inspiratory flow of inspiration gas inhaled by the subject, an expiratory flow of expiration gas exhaled by the subject, and the carbon dioxide content of at least the expiration gas, determining, for each breath in the sequence of breaths, a first parameter, ($\Delta F_A CO2$) related to the fraction of alveolar carbon dioxide ($F_A CO_2$) of the subject, a second parameter ($CaCO_2$) related to the carbon dioxide content of the arterial blood ($CaCO_2$) of the subject, and a third parameter ($VTCO_2$) related to carbon dioxide elimination ($VCO_2$) of the subject, based on the measured inspiratory flow, expiratory flow and carbon dioxide content, and determining said at least one physiological parameter (V, Q, $CvCO_2$) based on the correlation of the first ($\Delta F_A CO2$), second ($CaCO_2$) and third ($VTCO_2$) parameters in said sequence of breaths.

Preferably, the number of breaths in the analyzed sequence of breaths corresponds to the number of breaths in each cycle of the cyclic ventilation pattern. However, other alternatives are possible. For example, it would be possible to use a cyclic ventilation pattern wherein each cycle comprises five breaths, and to determine the unknown physiological parameter(s) by studying the correlation of the first, second and third parameters in a sequence of 10 breaths.

As discussed above, the changes in effective ventilation should preferably cause a change in the carbon dioxide content in the expiration gas exhaled by the subject of at least 0.5% during the analyzed sequence of breaths. Thus, in the preferred embodiment where the number of breaths in the analyzed sequence of breaths equals the number of breaths in each cycle of the cyclic ventilation pattern, the cyclic ventilation pattern should be such that the carbon dioxide content in the expiration gas exhaled by the subject changes with at least 0.5% during any sequence of breaths having the same length (i.e. number of breaths) as the cycles of the ventilation pattern.

In a preferred embodiment, there are five breaths in each cycle of the cyclic ventilation pattern. Preferably but not necessarily, the number of breaths of increased ventilation is higher than the number of breaths of decreased ventilation in each cycle of the cyclic ventilation pattern. In an exemplary embodiment, each cycle of the cyclic ventilation pattern comprises three breaths of increased ventilation and two breaths of decreased ventilation. In another embodiment, each cycle comprises four breaths of increased ventilation and one breath of decreased ventilation.

In a preferred embodiment the changes in effective ventilation are made by prolonging the inspiratory pause for breaths of decreased ventilation compared to the inspiratory pause for breaths of increased ventilation. For example, a suitable cyclic ventilation pattern may have cycles comprising three breaths of increased ventilation, each with a duration of three seconds and no inspiratory pause, and two breaths of decreased ventilation, each with a duration of three seconds and an inspiratory pause of four seconds. This means that the duration of the sequence of increased ventilation is 9 seconds (3×3 s), the duration of the sequence of decreased ventilation is 14 seconds (2×(3 s+4 s)), and the duration of each cycle in the cyclic ventilation pattern is 23 seconds (9 s+14 s). It has been found that for any given sequence of five consecutive breaths, this ventilation pattern causes a sufficient change in carbon dioxide content in the expiration gas exhaled by the subject.

Figure 4:
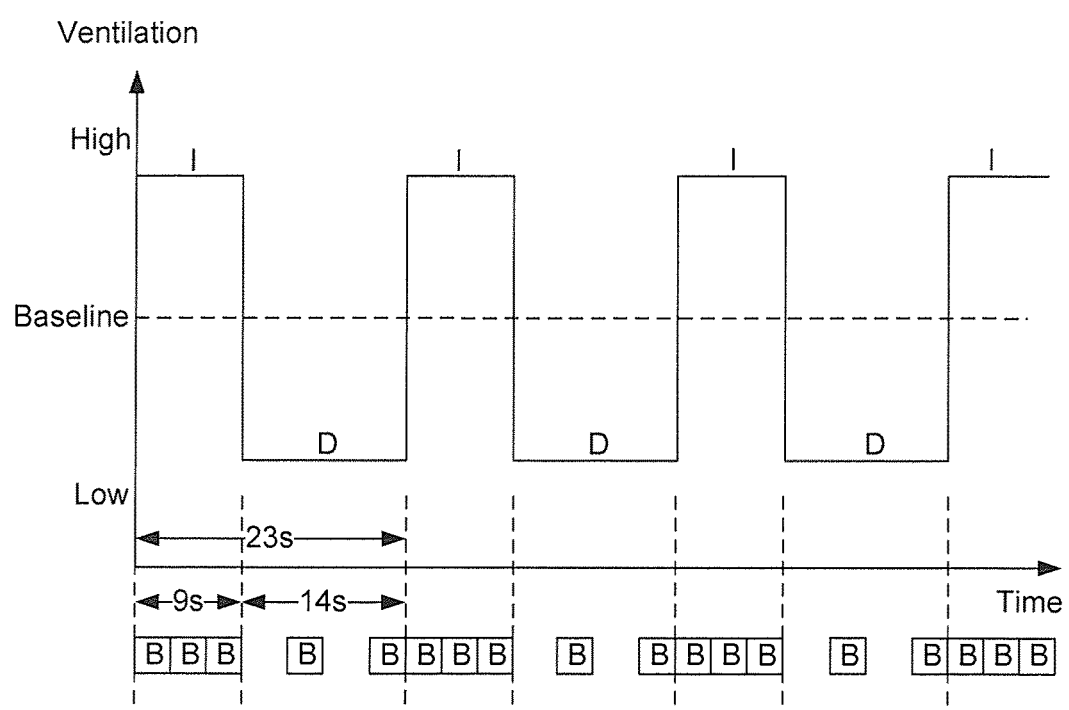
FIG. 4 illustrates a ventilation pattern that may be applied to a subject undergoing ventilatory treatment in order to determine parameters related to the effective lung volume, the cardiac output, and/or the carbon dioxide content of venous blood of the subject.

This exemplary cyclic ventilation pattern is illustrated in FIG. 4, in which the letter "I" indicates sequences of increased ventilation, the letter "D" indicates sequences of decreased ventilation, and the letter "B" indicates breaths in the sequences of increased and decreased ventilation. The effective respiratory rate using this cyclic ventilation pattern is 13 breaths per minute (($5/23$)×60).

Although modifications and changes may be suggested by those skilled in the art, it is the intention of the inventors to embody within the patent warranted hereon all changes and modifications as reasonably and properly come within the scope of his contribution to the art.

We claim as our invention:

1. A non-invasive method for simultaneously determining at least two physiological parameters related, respectively, to the effective lung volume and the cardiac output of a subject, the method comprising the steps of, during a sequence of respiratory cycles:

changing ventilation of a subject provided by a breathing apparatus, wherein the change of ventilation is performed by a control unit of the breathing apparatus and wherein the change in ventilation causes a substantial change in carbon dioxide content in expiration gas exhaled by the subject during the sequence of respiratory cycles;

after changing ventilation, measuring at least an expiratory flow of expiration gas exhaled by the subject, and measuring the carbon dioxide content of at least the expiration gas, wherein the expiratory flow of the expiration gas is measured by at least one flow sensor of a monitoring device, and the carbon dioxide content is measured by at least one gas analyzer of the monitoring device;

determining, for each respiratory cycle in the sequence of respiratory cycles, a first parameter related to the fraction of alveolar carbon dioxide of the subject, a second parameter related to the carbon dioxide content of the arterial blood of the subject, and a third parameter related to carbon dioxide elimination of the subject, wherein the determination of each of the first parameter, the second parameter, and the third parameter is performed by the control unit of the breathing apparatus and is based on the measured expiratory flow and the measured carbon dioxide content;

for each respiratory cycle in the sequence of respiratory cycles, the control unit inserts the determined values of the first, second and third parameters into a capnodynamic equation so as to form an overdetermined system of equations, wherein the simultaneous determination of the at least two physiological parameters is performed by the control unit, and the simultaneous determination of the at least two physiological parameters involves finding an approximate solution to the overdetermined system of equations; and continuously monitoring the at least two physiological parameters simultaneously determined by the control unit, wherein the control unit is a component of the monitoring device.

2. The method according to claim 1, wherein the step of determining said at least one physiological parameter comprises simultaneous determination of a physiological parameter related to the effective lung volume of the subject, a physiological parameter related to the cardiac output of the subject, and a physiological parameter related the carbon dioxide content of venous blood of the subject, the simultaneous determination of the physiological parameters being performed by the control unit of the breathing apparatus by finding the approximate solution to the overdetermined system of equations.

3. The method according to claim 1, wherein the capnodynamic equation describes a relationship between parameters relating to effective lung volume, cardiac output, carbon dioxide content of venous blood, fraction of alveolar carbon dioxide, carbon dioxide content of arterial blood and carbon dioxide elimination of a subject, so as to form the overdetermined system of equations.

4. The method according to claim 3, wherein said capnodynamic equation is:

$$V \cdot \Delta F_A CO_2 = \Delta t \cdot Q \cdot (CvCO_2 - CaCO_2) - VTCO_2$$

where V is the effective lung volume during the respiratory cycle, $\Delta F_A CO_2$ is the change in volume fraction of alveolar carbon dioxide during the respiratory cycle, $\Delta t$ is the duration in time of the respiratory cycle, Q is the effective pulmonary capillary blood flow during the respiratory cycle, $CvCO_2$ is the carbon dioxide content of venous blood during the respiratory cycle, $CaCO_2$ is the carbon dioxide content of arterial blood during the respiratory cycle, and $VTCO_2$ is the tidal volume elimination of carbon dioxide during the respiratory cycle.

5. The method according to claim 1, wherein the at least one physiological parameter is determined on a breath-by-breath basis by, for each respiratory cycle, replacing the values of the first, second and third parameters obtained during the oldest respiratory cycle in the sequence of respiratory cycles with the values obtained during the most recent respiratory cycle.

6. The method according to claim 1, wherein the step in which the at least a physiological parameter related to the effective lung volume of the subject is determined further comprises the steps of:
measuring also an inspiratory flow of inspiration gas inhaled by the subject,
calculating a difference in volume of inspired and expired gas in each respiratory cycle from the measured inspiratory and expiratory flows; and
determining an updated value of a current effective lung volume of the subject based on the determined physiological parameter and said differences.

7. The method according to claim 1, further comprising the steps of obtaining, prior to determination of the at least one physiological parameter, a priori information comprising at least one value of at least one of said physiological parameters using another method for determination of at least one of said physiological parameters, and using said a priori information in the determination of the at least one physiological parameter.

8. The method according to claim 1, further comprising the steps of determining an error in the determination of the at least one physiological parameter based on the correlation of the first, second and third parameters in the sequence of respiratory cycles, and generating an alarm signal if the error indicates that the correlation is weak.

9. The method according to claim 1, wherein the breathing apparatus is a ventilator or an anesthesia machine.

10. The method according to claim 1, wherein the substantial change in the carbon dioxide content in expiration gas exhaled by the subject is at least 0.5%.

11. A non-transitory, computer-readable data storage medium encoded with programming instructions for non-invasive determination of at least one physiological parameter related to the effective lung volume, the cardiac output, and/or the carbon dioxide content of venous blood of a subject, said storage medium being loaded into a processor of a breathing apparatus that also comprises at least one flow sensor of a monitoring device for measuring at least an expiratory flow of expiration gas exhaled by the subject, at least one gas analyzer of the monitoring device measuring the carbon dioxide content of at least the expiration gas exhaled by the subject, said programming instructions causing said processor to:

change ventilation of a subject provided by the breathing apparatus so as to cause a substantial change in carbon dioxide content in expiration gas exhaled by the subject during a sequence of respiratory cycles;

following the change in ventilation, process a measure of at least an expiratory flow of expiration gas exhaled by the subject, and process a measure of the carbon dioxide content of at least the expiration gas, wherein the expiratory flow of the expiration gas is measured by the at least one flow sensor, and the carbon dioxide content is measured by the at least one gas analyzer;

determine, for each respiratory cycle in the sequence of respiratory cycles, a first parameter related to the fraction of alveolar carbon dioxide of the subject, a second parameter related to the carbon dioxide content of the arterial blood of the subject, and a third parameter related to carbon dioxide elimination of the subject, wherein the determination of each of the first parameter, the second parameter, and the third parameter is based on the measured expiratory flow and the measured carbon dioxide content; and for each respiratory cycle in the sequence of respiratory cycles, the processor inserts the determined values of the first, second and third parameters into a capnodynamic equation so as to form an overdetermined system of equations, wherein the determination of the at least one physiological parameter is performed by the processor, and the determination of the at least one physiological parameter involves finding an approximate solution to the overdetermined system of equations; and calculate an error indicative of uncertainty in the determination of the at least one physiological parameter; and cause an alarm signal to be generated by the monitoring device when the error exceeds a predetermined threshold value; and provide continuous monitoring of the at least one physiological parameter determined by the processor, wherein the processor is a component of the monitoring device.

12. The non-transitory, computer-readable data storage medium encoded with programming instructions according to claim 11, wherein the breathing apparatus is a ventilator or an anesthesia machine.

13. The non-transitory, computer-readable data storage medium according to claim 11, wherein the programming instructions cause the processor to calculate the error such that the error depends on the correlation between the first, second and third parameters in the respiratory cycles of the sequence of respiratory cycles.

14. A breathing apparatus adapted to provide a non-invasive determination of at least one physiological parameter related to the effective lung volume, the cardiac output, and/or the carbon dioxide content of venous blood of a subject, the breathing apparatus comprising:

a breathing assist apparatus selected from the group consisting of a ventilator and an anesthesia machine; and a monitoring device, wherein the monitoring device comprises
at least one flow sensor disposed to measure at least an expiratory flow of expiration gas exhaled by the subject, during a sequence of respiratory cycles;
at least one gas analyzer disposed to measure the carbon dioxide content of at least the expiration gas; and a control unit configured to control ventilation of the subject provided by the breathing assist apparatus and to determine, for each respiratory cycle in the sequence of respiratory cycles following a ventilation change by the control unit that causes a substantial change in the carbon dioxide content in the expiration gas, a first parameter related to the fraction of alveolar carbon dioxide of the subject, a second parameter related to the carbon dioxide content of the arterial blood of the subject, and a third parameter related to carbon dioxide elimination of the subject, wherein the determination of each of the first parameter, the second parameter, and the third parameter is based on the measured expiratory flow provided by the at least one flow sensor and the measured carbon dioxide content provided by the at least one gas analyzer, and the control unit is configured to, for each respiratory cycle in the sequence of respiratory cycles, insert the determined values of the first, second and third parameters into a capnodynamic equation so as to form an overdetermined system of equations, wherein the determination of the at least one physiological parameter by the control unit involves finding an approximate solution to the overdetermined system of equations, and the control unit is configured to provide non-invasive continuous monitoring of the at least one determined physiological parameter during respiratory treatment provided by the breathing assist apparatus.

15. The breathing apparatus according to claim 14, wherein said control unit is configured to operate said breathing apparatus to provide a ventilatory treatment to the subject.

16. The breathing apparatus according to claim 15, wherein the control unit is configured to cause a change in the effective ventilation of the subject to cause the carbon dioxide content of the expiration gas exhaled by the subject to vary in a range of 0.5%-1% during said sequence of respiratory cycles.

17. The breathing apparatus according to claim 16, wherein the control unit is configured to change the effective ventilation of the subject to deliver a ventilation pattern with alternating sequences of breaths of increased ventilation and breaths of decreased ventilation to the subject.

18. A non-invasive method for determining at least one physiological parameter related to the effective lung volume, the cardiac output, and/or the carbon dioxide content of venous blood of a subject, the method comprising the steps of, during a sequence of respiratory cycles:
changing ventilation of a subject provided by a breathing apparatus, wherein the change of ventilation is performed by a control unit of the breathing apparatus and wherein the change in ventilation causes a substantial change in carbon dioxide content in expiration gas exhaled by the subject during the sequence of respiratory cycles;
after changing ventilation, measuring at least an expiratory flow of expiration gas exhaled by the subject, and measuring the carbon dioxide content of at least the expiration gas, wherein the expiratory flow of the expiration gas is measured by at least one flow sensor of a monitoring device, and the carbon dioxide content is measured by at least one gas analyzer of the monitoring device;
determining, for each respiratory cycle in the sequence of respiratory cycles, a first parameter related to the fraction of alveolar carbon dioxide of the subject, a second parameter related to the carbon dioxide content of the arterial blood of the subject, and a third parameter related to carbon dioxide elimination of the subject, wherein the determination of each of the first parameter, the second parameter, and the third parameter is performed by the control unit of the breathing apparatus and is based on the measured expiratory flow and the measured carbon dioxide content;
for each respiratory cycle in the sequence of respiratory cycles, the control unit inserts the determined values of the first, second and third parameters into a capnodynamic equation so as to form an overdetermined system of equations, wherein the determination of the at least one physiological parameter is performed by the control unit, and the determination of the at least one physiological parameter involves finding an approximate solution to the overdetermined system of equations; and
calculating an error indicative of uncertainty in the determination of the at least one physiological parameter, wherein the control unit calculates the error and causes an alarm signal to be generated by the monitoring device when the error exceeds a predetermined threshold value, wherein the control unit is a component of the monitoring device and the monitoring device continuously monitors the at least one physiological parameter determined by the control unit.

19. The method according to claim 18, wherein the error is calculated such that the error depends on the correlation between the first, second and third parameters in the respiratory cycles of the sequence of respiratory cycles.

20. A non-transitory, computer-readable data storage medium encoded with programming instructions for non-invasive and simultaneous determination of at least two physiological parameters related, respectively, to the effective lung volume and the cardiac output of a subject, said storage medium being loaded into a processor of a breathing apparatus that also comprises at least one flow sensor of a monitoring device for measuring at least an expiratory flow of expiration gas exhaled by the subject, and at least one gas analyzer of the monitoring device for measuring the carbon dioxide content of at least the expiration gas exhaled by the subject, said programming instructions causing said processor to:
change ventilation of a subject provided by the breathing apparatus so as to cause a substantial change in carbon dioxide content in expiration gas exhaled by the subject during a sequence of respiratory cycles;
following the change in ventilation, process a measure of at least an expiratory flow of expiration gas exhaled by the subject, and process a measure of the carbon dioxide content of at least the expiration gas, wherein the expiratory flow of the expiration gas is measured by the at least one flow sensor, and the carbon dioxide content is measured by the at least one gas analyzer;
determine, for each respiratory cycle in the sequence of respiratory cycles, a first parameter related to the fraction of alveolar carbon dioxide of the subject, a second parameter related to the carbon dioxide content of the arterial blood of the subject, and a third parameter related to carbon dioxide elimination of the subject, wherein the determination of each of the first parameter, the second parameter, and the third parameter is based on the measured expiratory flow and the measured carbon dioxide content; and
for each respiratory cycle in the sequence of respiratory cycles, the processor inserts the determined values of the first, second and third parameters into a capnodynamic equation so as to form an overdetermined system of equations, wherein the simultaneous determination of the at least two physiological parameters is performed by the processor, and the determination of the at least two physiological parameters involves finding an approximate solution to the overdetermined system of equations; and provide continuous monitoring of the at least two physiological parameters determined by the processor, wherein the processor is a component of the monitoring device.

21. A breathing apparatus adapted to provide a non-invasive determination of at least one physiological parameter related to the effective lung volume, the cardiac output, and/or the carbon dioxide content of venous blood of a subject, the breathing apparatus comprising:
  a breathing assist apparatus selected from the group consisting of a ventilator and an anesthesia machine; and
  a monitoring device, wherein the monitoring device comprises
    at least one flow sensor disposed to measure at least an expiratory flow of expiration gas exhaled by the subject, during a sequence of respiratory cycles;
    at least one gas analyzer disposed to measure the carbon dioxide content of at least the expiration gas; and
    a control unit configured to control ventilation of the subject provided by the breathing assist device and to determine, for each respiratory cycle in the sequence of respiratory cycles following a ventilation change by the control unit that causes a substantial change in the carbon dioxide content in the expiration gas, a first parameter related to the fraction of alveolar carbon dioxide of the subject, a second parameter related to the carbon dioxide content of the arterial blood of the subject, and a third parameter related to carbon dioxide elimination of the subject, wherein the determination of each of the first parameter, the second parameter, and the third parameter is based on the measured expiratory flow provided by the at least one flow sensor and the measured carbon dioxide content provided by the at least one gas analyzer, and the control unit is configured to, for each respiratory cycle in the sequence of respiratory cycles, insert the determined values of the first, second and third parameters into a capnodynamic equation so as to form an overdetermined system of equations, wherein the determination of the at least one physiological parameter by the control unit involves finding an approximate solution to the overdetermined system of equations, the control unit further being configured to calculate an error indicative of uncertainty in the determination of the at least one physiological parameter, and cause an alarm signal to be generated by the monitoring device when the error exceeds a predetermined threshold value.

22. The breathing apparatus according to claim 21, wherein the control unit is configured to provide non-invasive continuous monitoring of the at least one determined physiological parameter during respiratory treatment provided by the breathing assist apparatus.

23. The breathing apparatus according to claim 21, wherein the control unit is configured to calculate the error such that the error depends on the correlation between the first, second and third parameters in the respiratory cycles of the sequence of respiratory cycles.

24. A breathing apparatus adapted to provide non-invasive and simultaneous determination of at least two physiological parameters related, respectively, to the effective lung volume and the cardiac output of a subject, the breathing apparatus comprising:
  a breathing assist apparatus selected from the group consisting of a ventilator and an anesthesia machine; and
  a monitoring device, wherein the monitoring device comprises
    at least one flow sensor disposed to measure at least an expiratory flow of expiration gas exhaled by the subject, during a sequence of respiratory cycles;
    at least one gas analyzer disposed to measure the carbon dioxide content of at least the expiration gas; and
    a control unit configured to control ventilation of the subject provided by the breathing assist apparatus and to determine, for each respiratory cycle in the sequence of respiratory cycles following a ventilation change by the control unit that causes a substantial change in the carbon dioxide content in the expiration gas, a first parameter related to the fraction of alveolar carbon dioxide of the subject, a second parameter related to the carbon dioxide content of the arterial blood of the subject, and a third parameter related to carbon dioxide elimination of the subject, wherein the determination of each of the first parameter, the second parameter, and the third parameter is based on the measured expiratory flow provided by the at least one flow sensor and the measured carbon dioxide content provided by the at least one gas analyzer, and the control unit is configured to, for each respiratory cycle in the sequence of respiratory cycles, insert the determined values of the first, second and third parameters into a capnodynamic equation so as to form an overdetermined system of equations, wherein the simultaneous determination of the at least two physiological parameters by the control unit involves finding an approximate solution to the overdetermined system of equations, and the control unit is configured to provide non-invasive continuous monitoring of the at least two simultaneously determined physiological parameters during respiratory treatment provided by the breathing assist apparatus.

* * * * *